United States Patent [19]

Bergthaller et al.

[11] 4,297,439
[45] Oct. 27, 1981

[54] PRODUCTION OF PHOTOGRAPHIC SILVER HALIDE EMULSION

[75] Inventors: Peter Bergthaller, Cologne; Wilhelm Saleck, Bergisch-Gladbach; Otto Lapp, Leverkusen; Bruno Mücke, Bergisch-Gladbach, all of Fed. Rep. of Germany

[73] Assignee: AGFA-Gevaert AG, Leverkusen, Fed. Rep. of Germany

[21] Appl. No.: 42,974

[22] Filed: May 29, 1979

[30] Foreign Application Priority Data

Jun. 2, 1978 [DE] Fed. Rep. of Germany ....... 2824249

[51] Int. Cl.³ ............................ G03C 1/02; G03C 1/28
[52] U.S. Cl. ................................ 430/434; 23/295 G; 430/569; 430/611
[58] Field of Search ................... 96/107, 108, 94 R; 430/569, 611, 434; 23/295 G

[56] References Cited

U.S. PATENT DOCUMENTS

| | | | |
|---|---|---|---|
| 3,021,215 | 2/1962 | Williams et al. | 96/107 X |
| 3,062,646 | 11/1962 | Dann et al. | 96/107 X |
| 3,271,157 | 9/1966 | McBride | 96/108 X |
| 3,531,289 | 9/1970 | Wood | 430/569 |
| 3,574,628 | 4/1971 | Wood | 430/567 |
| 3,637,391 | 1/1972 | Saleck et al. | 430/569 |
| 3,767,413 | 10/1973 | Miller | 430/569 |
| 3,790,387 | 2/1974 | Musliner | 96/94 R |
| 3,915,714 | 10/1975 | Saleck et al. | 96/107 |
| 4,046,576 | 9/1977 | Terwilliger et al. | 96/94 R X |
| 4,057,429 | 11/1977 | De Brabandere et al. | 430/569 |

FOREIGN PATENT DOCUMENTS

| | | | |
|---|---|---|---|
| 1068244 | 11/1959 | Fed. Rep. of Germany . | |
| 2159379 | 11/1971 | Fed. Rep. of Germany | 96/94 R |
| 2307242 | 8/1976 | France . | |
| 348961 | 11/1960 | Switzerland . | |
| 1416455 | 12/1975 | United Kingdom | 96/94 R |

*Primary Examiner*—Edward C. Kimlin
*Attorney, Agent, or Firm*—Connolly and Hutz

[57] ABSTRACT

New thioethers of the formula

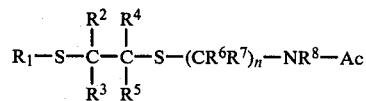

in which Ac represents an acyl radical have been found. They are useful for producing silver halide emulsions for photographic materials.

8 Claims, No Drawings

PRODUCTION OF PHOTOGRAPHIC SILVER HALIDE EMULSION

This invention relates to new thioethers and to their use in photographic materials. More particularly, the invention relates to a process for the production of photographic materials comprising at least one silver halide emulsion layer, in which the silver halides are precipitated by reacting a water-soluble silver salt with an alkali halide in a binder medium in the presence of the thioethers according to the invention.

There are various known processes for producing photosensitive silver halide emulsions. The properties of these emulsions and determined above all by the crystal size of the silver halide grains and their grain size distribution. In special cases, the crystal habit is also an important factor.

The size of the silver halide crystals is determined above all by the so-called Ostwald ripening, in which the larger crystals grow at the expense of smaller crystals of the same composition. An important parameter in Ostwald ripening is the excess of halide ions which are known to allow the silver ions to be transported from the smaller crystals to the larger crystals by complex formation.

It is also known how to produce monodisperse silver halide emulsions, i.e. emulsions having an extremely narrow grain size distribution. In the production of monodisperse emulsions of this type, grain growth such as occurs in Ostwald ripening is avoided. However, it is not satisfactorily possible by conventional processes to limit the number of silver halide nuclei formed during precipitation to such an extent that, from the outset, silver halide nuclei are only formed in a quantity commensurate with the quantity of silver halide crystals required.

It is known that Ostwald ripening in the production of heterodisperse emulsions and also crystal growth in the production of monodisperse emulsions can be influenced by the addition of thioethers. For example, German Auslegeschrift No. 1,904,148 describes a process for the production of fogged direct-positive silver halide emulsions in the presence of certain thioethers. Unfortunately, known thioethers have the disadvantage that they can give rise undesirably to fogging or that they are effective in only very large quantities. Accordingly, one object of the present invention is to provide new thioethers which do not have the disadvantages of known thioethers.

New thioethers having the following structure have now been found:

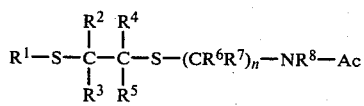

in which:

$R^1$ represents an aliphatic or cycloaliphatic aryl or aralkyl radical;

$R^2$, $R^3$, $R^4$, $R^5$, $R^6$ and $R^7$ may be the same or different and represent hydrogen or alkyl;

$R^8$ represents hydrogen;

Ac is an acyl radical and n is an integer with a value of at least one.

Furthermore it has now been found that the properties of photographic materials can be distinctly improved with thioethers corresponding to formula I above.

Furthermore, a process for the production of photographic materials containing at least one silver halide emulsion layer in which the silver halide emulsion is produced in the presence of at least one thioether corresponding to formula I have been found.

A further object of the present invention is a photographic material containing at least one silver halide emulsion layer, characterised in that it contains a thioether corresponding to the formula I.

A further object of the present invention is a process for the production of photographic images by exposing a photographic material containing at least one photosensitive silver halide emulsion layer to form an image, followed by development and further suitable processing characterised in that the silver halide grains of the silver halide emulsion layer are produced in the presence of a thioether corresponding to formula I.

In the context of formula I, acyl radicals are in particular acyl radicals of the type derived from aliphatic or aromatic dicarboxylic or sulphocaroxylic acids, carbonic acid monoesters and carbamic acids. Examples of acyl radicals such as these are succinoyl, carbamoyl, phenyl carbamoyl, sulphonamidocarbonyl and acylaminocarbonyl radicals.

The thioethers preferably have the following structure:

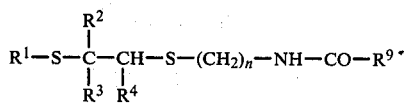

in which:

$R^1$ represents an aliphatic or cycloaliphatic radical containing at most 6 carbon atoms or an aralkyl radical containing at most 8 carbon atoms;

$R^2$, $R^3$ and $R^4$ may be the same or different and represent hydrogen, an alkyl radical containing from 1 to 7 carbon atoms, particularly a methyl radical;

n=2 or 3;

$R^9$ represents $-NH-R^{10}$; $-R^{11}-COOM$ or $R^{11}-SO_3 M$;

M represents a metal ion, particularly an alkali or alkaline earth metal ion;

$R^{10}$ represents hydrogen, an alkyl radical containing from 1 to 3 carbon atoms; an alkoxy alkyl, hydroxy alkyl, alkane sulphonyl or acyl radical;

$R^{11}$ represents an aliphatic, cycloaliphatic or aromatic radical which may be additionally substituted, in particular by an alkyl thio group, and/or $R^1$ together with $R^2$ and optionally $R^3$ represent the radical required to complete a heterocyclic membered ring particularly a 5- or 6-membered ring and/or $R^4$ together with $R^2$ or $R^3$ represent the radical required to complete a cycloaliphatic ring, particularly a 5- or 6-membered ring, quite particularly a cycloaliphatic membered ring, particularly a cyclohexane ring.

It has also been found that the thioethers corresponding to formula I above can be produced in known manner from the corresponding amines corresponding to the formula:

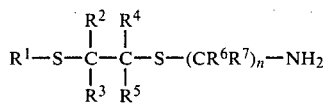

$$R^1-S-\underset{\underset{R^3}{|}}{\overset{\overset{R^2}{|}}{C}}-\underset{\underset{R^5}{|}}{\overset{\overset{R^4}{|}}{C}}-S-(CR^6R^7)_n-NH_2 \quad \text{III}$$

in which n and $R^1$, $R^2$, $R^3$, $R^4$, $R^5$, $R^6$ and $R^7$ have the same meanings as in formula I.

To this end, the amines of formula III are reacted with alkali cyanates, oxazolidin-2-ones, acyl isocyanates, alkyl isocyanates, alkane sulphonyl isocyanates, dicarboxylic acid anhydrides or sulphocarboxylic acid anhydrides.

Solvents suitable for the reaction with alkali cyanates are, in particular, water, alcohols, acetone and acetonitrile or mixtures thereof, the amines being used in the form of readily soluble salts, for example, hydrochlorides, sulphates, perchlorates, nitrates or alkane sulphonates. For the other reactions, the amines are preferably reacted in the form of their free bases in preferably non-aqueous solutions, for example in ethylacetate, dichloromethane, acetonitrile, 1,2-dichloroethane or dimethyl formamide.

The amines corresponding to formula III are preferably produced from amines corresponding to the following formula:

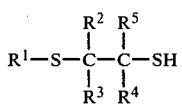

$$R^1-S-\underset{\underset{R^3}{|}}{\overset{\overset{R^2}{|}}{C}}-\underset{\underset{R^4}{|}}{\overset{\overset{R^5}{|}}{C}}-SH \quad \text{IV}$$

in which $R^1$, $R^2$, $R^3$, $R^4$ and $R^5$ have the same meanings as in formula I.

Reactions such as these are described in German Offenlegungsschrift No. 1,904,149. Preferred reactants are aziridine, ammonium methyl sulphate, chloroethylamine, bromoethylamine or 3-chloropropylamine. The reaction is preferably carried out in a neutral or alkaline medium. Particularly suitable compounds of formula III are listed in Table 1 below:

TABLE 1

| Subst. No. | Compound |
|---|---|
| 1.1 | $CH_3-S-CH_2CH_2-S-CH_2CH_2-NH_2$ |
| 1.2 | $CH_3-S-\underset{\underset{CH_3}{|}}{\overset{\overset{CH_3}{|}}{C}}-CH_2-S-CH_2CH_2-NH_2$ |
| 1.3 | $CH_3-S-CH_2CH_2-S-CH_2CH_2CH_2-NH_2$ |
| 1.4 | $C_2H_5-S-CH_2CH_2-S-CH_2CH_2-NH_2$ |
| 1.5 | $C_2H_5-S-\underset{\underset{CH_3}{|}}{CH}-CH_2-S-CH_2CH_2-NH_2$ |
| 1.6 | $C_2H_5-S-\underset{\underset{CH_3}{|}}{CH}-\underset{\underset{CH_3}{|}}{CH}-S-CH_2CH_2-NH_2$ |
| 1.7 | $C_2H_5-S-CH-CH-S-CH_2CH_2-NH_2$ (with cyclohexane ring: $CH_2-CH_2-CH_2-CH_2$) |
| 1.8 | $C_2H_5-S-CH_2CH_2-S-CH_2CH_2CH_2-NH_2$ |
| 1.9 | $CH_3-(CH_2)_2-S-CH_2CH_2-S-CH_2CH_2-NH_2$ |
| 1.10 | $\underset{CH_3}{\overset{CH_3}{\diagdown}}CH-S-CH_2CH_2-S-CH_2CH_2-NH_2$ |
| 1.11 | $\underset{CH_3}{\overset{CH_3}{\diagdown}}CH-S-\underset{\underset{CH_3}{|}}{CH}-CH_2-S-CH_2CH_2-NH_2$ |
| 1.12 | $CH_3-CH_2CH_2CH_2-S-CH_2CH_2-S-CH_2CH_2-NH_2$ |
| 1.13 | phenyl-$CH_2-S-CH_2CH_2-S-CH_2CH_2-NH_2$ |
| 1.14 | thiophene-$CH_2-S-CH_2CH_2-NH_2$ |

Particularly suitable isocyanates are methyl isocyanate, ethyl isocyanate, 2-methoxy ethyl isocyanate, methane sulphonyl isocyanate, preferably in masked form as N-methane sulphonyl-O-ethyl urethane, ethane sulphonyl isocyanate, propane sulphonyl isocyanate and acetyl isocyanate.

Particularly suitable dicarboxylic acid anhydrides are succinic acid anhydride, glutaric acid anhydride, 2-ethyl mercapto succinic acid anhydride, maleic acid anhydride, hexahydrophthalic acid anhydride, 1,2,3,6-tetrahydrophthalic acid anhydride, phthalic acid anhydride, pyromellitic acid anhydride, naphthalic acid anhydride, 4-sulphonaphthalic acid anhydride, and diglycolic acid anhydride.

Particularly suitable sulphocarboxylic acid anhydrides are 3H-2,1-benzoxthiol-3-one-1,1-dioxide, (2-sulphobenzoic acid endoanhydride) and 3-sulphopropionic acid anhydride.

Particularly suitable thioethers of general formula I are listed in Tables 2 and 3 below and correspond to the following structures:

$$R^1-S-CH_2-CH_2-S-CH_2CH_2-NH-COR^9 \quad \text{V}$$

$$R^1-CR^2H\ CR^4H-S-(CH_2)_n-NH-CO-R^9 \quad \text{VI}$$

in which $R^1$, $R^2$, $R^4$, $R^9$ and n have the meaning indicated under structure I and especially under structure II.

TABLE 2

$R^1-S-CH_2CH_2-S-CH_2CH_2-NH-CO-R^9$

| Subst. No. | $R^1$ | $R^9$ | m p (°K.) |
|---|---|---|---|
| 2.1 | $-CH_3$ | $-CH_2CH_2-COOH$ | 381–82° |
| 2.2 | $-CH_3$ | $-NH_2$ | 375–76° |
| 2.3 | $-CH_3$ | $-CH=CH-COOH$ | 348° |
| 2.4 | $-CH_3$ | 2-carboxyphenyl (benzene ring with COOH) | 391–92° |
| 2.5 | $-CH_3$ | 2-carboxycyclohexyl | 379–80° |
| 2.6 | $-C_2H_5$ | $-NH_2$ | 373–74° |
| 2.7 | $-C_2H_5$ | $-NH-SO_2CH_3$ | 377° |
| 2.8 | $-C_2H_5$ | $-CH_2CH_2-COOH$ | 392–93° |
| 2.9 | $-C_2H_5$ | $-CH_2CH_2CH_2-COOH$ | 343° |
| 2.10 | $-C_2H_5$ | $-CH=CH-COOH$ | 342–43° |
| 2.11 | $-C_2H_5$ | $C_2H_5$-cyclopropyl-COOH | 331–33° |

TABLE 2-continued $R^1-S-CH_2CH_2-S-CH_2CH_2-NH-CO-R^9$

| Subst. No. | $R^1$ | $R^9$ | m p (°K.) |
|---|---|---|---|
| 2.12 | —C$_2$H$_5$ | ![cyclohexane with COOH and H] | 367–68° |
| 2.13 | —C$_2$H$_5$ | (phenyl)-COOH (ortho) | 391–92° |
| 2.14 | —C$_2$H$_5$ | —NH—SO$_2$—(phenyl)—CH$_3$ | 327° |
| 2.15 | —C$_2$H$_5$ | (naphthyl)-COOH | 406–07° |
| 2.16 | —C$_2$H$_5$ | —NHCH$_3$ | 348° |
| 2.17 | CH$_3$—CH$_2$—CH$_2$— | —CH$_2$CH$_2$—COOH | 396–97° |
| 2.18 | CH$_3$—CH$_2$—CH$_2$— | —NH$_2$ | 356–57° |
| 2.19 | CH$_3$—CH$_2$—CH$_2$— | (cyclohexane with COOH and H) | 340–41° |
| 2.20 | CH$_3$—CH$_2$—CH$_2$— | (phenyl)-COOH | 382–83° |
| 2.21 | (CH$_3$)$_2$CH— | —NH$_2$ | 369° |
| 2.22 | (CH$_3$)$_2$CH— | —CH$_2$CH$_2$—COOH | 363° |
| 2.23 | (CH$_3$)$_2$CH— | (phenyl)-COOH | 387–88° |
| 2.24 | H$_3$C—(CH$_2$)$_3$— | —NH$_2$ | 356–57° |
| 2.25 | H$_3$C—(CH$_2$)$_3$— | —CH$_2$CH$_2$—COOH | 376–77° |
| 2.26 | (cyclohexyl)- | —NH$_2$ | 383–84° |
| 2.27 | (cyclohexyl)- | —NH—SO$_2$—CH$_3$ | 387–89° |

TABLE 3

| Subst. No. | Formula | m p (°K.) |
|---|---|---|
| 3.1 | $C_2H_5-S-CH(CH_3)-CH_2-S-CH_2-CH_2-NH-CO-$(naphthyl with HOOC) | 390–91° |
| 3.2 | $(CH_3)_2-CH-S-CH(CH_3)-CH_2-S-CH_2-CH_2-NH-CO-CH_2-CH_2-COOH$ | 391–92° |
| 3.3 | (thiophene)-$CH_2-S-CH_2-CH_2-NH-CO-NH_2$ | 383° |
| 3.4 | (thiophene)-$CH_2-S-CH_2-CH_2-NH-CO-CH_2-CH_2-COOH$ | 372° |
| 3.5 | $C_2H_5-S-$(phenylene)$-S-CH_2-CH_2-NH-CO-CH_2-CH_2-COOH$ | 394–95° |
| 3.6 | $C_2H_5-S-CH_2-CH_2-S-CH_2-CH_2-CH_2-NH-CO-NH_2$ | 343° |
| 3.7 | $C_2H_5-S-CH_2-CH_2-S-CH_2-CH_2-CH_2-NH-CO-CH_2-CH_2-COOH$ | 385° |
| 3.8 | $C_2H_5-S-CH_2-CH_2-S-CH_2-CH_2-CH_2-NH-CO-$(phenyl-COOH) | 403° |
| 3.9 | $C_2H_5-S-CH_2-CH_2-S-CH_2-CH_2-NH-CONH-CO-CH_3$ | |
| 3.10 | $C_2H_5-S-CH_2-CH_2-S-CH_2-CH_2-NH-CONH-CH_2-CH_2-OH$ | |

The production of the starting amines and of the compounds according to the invention is representatively described in the following:

Compound 1.9: 1-amino-3,6-dithianonane 76.4 g (0.164 mole) of 1-hydroxy-3-thiahexane, produced from propane-1-thiol and 2-chloroethanol in the presence of the equivalent quantity of sodium hydroxide were boiled under reflux for 2 hours with 50 g of thiourea and 77 g of 37% hydrochloric acid. After cooling, 32 g (0.8 mole) of sodium hydroxide in 60 ml of water were added to the clear solution of the isothiuronium salt. Thereafter the mixture was heated for 30 minutes on a steam bath. The 1-mercapto-3-thiahexane precipitated was separated off in a separation funnel and was dissolved under nitrogen in a solution of 68 g (1.7 moles) of sodium hydroxide in 130 ml of water accommodated in a three-necked flask. A total of 74.5 g of 2-chloroethylamine hydrochloride in 200 ml of water was added dropwise to the resulting solution at 333° K. After 1 hour on a steam bath, the amine phase precipitated was separated off with ether (300 ml), dried with 40 g of KOH flakes, concentrated by evaporation and fractionated in vacuo.

Yield: 96 g (84% of the theoretical); b.p. (1.7 mb): 377° to 378° K.; $n_D^{26}$: 1,5272.

Compound 1.8: 1-amino-4,7-dithianonane 106 g (1 mole) of 1-hydroxy-3-thiapentane were boiled under reflux for 3 hours with 76 g (1 mole) of thiourea and 110 g (1.1 mole) of 37% hydrochloric acid. A solution of 68 g (1.21 moles) of potassium hydroxide in 100 ml of water was then added dropwise with stirring at 313° to 323° K. After heating for 40 minutes to 363° K., the 3-thiapentane-1-thiol precipitated was separated off in a separation funnel and dissolved under nitrogen at 303° to 313° K. in 400 g of 40% KOH (2.85 moles of KOH) accommodated in a 1000 ml three-necked flask. A solution of 130 g of 3-chloropropylamine hydrochloride (1 mole) in 160 ml of water was then added dropwise with stirring at 343° K. After stirring for another 3 hours at 363° K., the mixture was cooled to 323° K. and separated in a separation funnel. The oil phase was fractionated in vacuo twice.

Yield: 105 g (58% of the theoretical). b.p.$_{(3\ mb)}$: 388°–393° K.; $n_D^{25}$: 1.5290.

Compound 1.7:
1-amino-4,5-tetramethylene-3,6-dithiaoctane

This compound was produced in the following stages:

(a) 2-ethylmercapto cyclohexanol

Following the addition of 4 ml of DBN (1,5-diazabicyclo-[4,3,0]-non-5-ene), 98.1 g (1 mole) of cyclohexane oxide (Aldrich) were added dropwise to 65 g of ethane thiol (1.05 moles) in 300 ml of methanol. The mixture was kept under reflux overnight in a steam bath, the reflux temperature rising from 325° K. to 338° K. After adjustment to pH ~ 8 with carbon dioxide, the methanol was distilled off and the residue was fractionated in vacuo.

Yield: 155 g (97% of the theoretical).

(b) 2-ethylmercapto cyclohexane thiol 154 g (0.96 mole) of 3-ethyl mercapto cyclohexanol, 76 g of thiourea (1 mole) and 150 ml of concentrated hydrochloric acid were kept under reflux for 3 hours. The isothiuronium salt solution was separated off from oily secondary products in a separation funnel and then heated with 70 g of NaOH (1.75 mole) in 100 ml of water for 1 hour in a steam bath. Carbon dioxide was added for neutralisation, the mercaptan phase was separated off in the separation funnel and fractionated in vacuo.

Yield: 110 g (65% of theoretical); b.p.$_{(3.5\ mb)}$: 371°–376° K.

(c) 1-amino-4,5-tetramethylene-3,6-dithiaoctane 110 g (0.625 mole) of 2-ethyl mercapto cyclohexane thiol were taken up under nitrogen in a solution of 107.5 g of potassium hydroxide (1.92 moles) in 110 ml of water. Following the addition of 110 ml of methanol, a solution of 74.2 g (0.64 mole) of 2-chloroethylamine hydrochloride in 80 ml of water was added dropwise at 328° to 338° K. After 3 hours on a steam bath, the mixture was cooled, the amine phase was taken up in toluene and dried over sodium chloride, the toluene was removed in vacuo and the residue fractionated in vacuo.

Yield: 106 g (77% of theoretical). b.p.$_{(4.5\ mb)}$: 420°–425° K.

Compound 1.14: 1-amino-4-(2-thienyl)-3-thiabutane

This compound was produced in the following stages:

(a) 2-thienyl methane thiol 87 g (0.76 mole) of 2-thienyl methanol, 58 g (0.76 mole) of thiourea and 70 ml of concentrated hydrochloric acid were heated for 1 hour on a steam bath. Following the addition of 33 g (0.825 mole) of sodium hydroxide in 40 ml of water, the mixture was kept on the steam bath for 20 minutes and separated in a separation funnel.

(b) 1-amino-4-(2-thienyl)-3-thiabutane

The crude product from (a) was taken up under nitrogen in a solution of 128 g of potassium hydroxide (2.3 moles) in 150 ml of water. A solution of 88.2 g (0.76 mole) of 2-chloroethyl amine hydrochloride in 100 ml of water was then added dropwise with stirring at 323° K. After 3 hours on a steam bath, the reaction mixture was taken up with 200 ml of toluene, the toluene phase was washed with 200 ml of water, dried with sodium chloride, concentrated and fractionated in vacuo.

Yield: 65 g (49% of the theoretical); b.p.$_{(8\ mb)}$: 414°–425° K.

Compound 2.2: N-(3,6-dithia)-heptyl urea 15.1 (0.1 mole) of 1-amino-3,6-dithiaheptane were dissolved in 10% hydrochloric acid, the resulting solution having a pH-value of 4. 8.9 g (0.11 mole) of potassium cyanate in 20 ml of water were added to this solution. The solution heated up and precipitated an oil. After heating for 30 minutes on a steam bath, the reaction mixture was left to cool and the supernatant liquid was poured off from the crystallised product which was then recrystallised once from methanol-water (1:1) and once from ethyl acetate.

Yield: 15.2 g (78% of the theoretical) m.p. 375°–376° K.

Analysis: calc. a. $C_6H_{14}N_2OS_2$; C: 37.09; H: 7.26; S: 33.00; obsvd. C: 36.8; H: 7.40; S: 32.69.

Compound 2.7: N-(3,6-dithiaoctyl)-N'-methane sulphonyl urea 16.5 g (0.1 mole) of 1-amino-3,6-dithiaoctane, produced in accordance with DE-OS No. 1,904,149, and 17 g of N-methane sulphonyl-o-ethyl urethane, produced in accordance with Cassaday and Ainsworth, J. Org. Chem. 23, 923–926 (1958), were kept for 2 hours at 403° K. in an oil bath, the ethanol eliminated being blown out with nitrogen. After cooling, the crystallised product was recrystallised twice from ethyl acetate.

Yield: 15 g

Analysis: calcd. a. $C_8H_{18}N_2O_3S_3$; C: 33.55; H: 6.33; S: 33.58; obsvd. C: 33.8; H: 6.5; S: 33.6.

Compound 2.8: N-(3,6-dithiaoctyl)-succinamido acid 16.5 g of 1-amino-3,6-dithiaoctane were added to a solution of 11.0 g of succinic acid anhydride in 60 ml of dichloroethane. The temperature rose spontaneously to 343° K. After cooling in an ice bath, the crystallised product was isolated by filtration under suction and recrystallised twice from ethylacetate/isopropanol (3:1).

Yield: 18.6 g (70% of the theoretical).

Analysis: calc. a. $C_{10}H_{19}NO_3S_2$ C: 45.26; H: 7.16; S: 24.16; obsvd.: C: 45.5; H: 7.15; S: 24.15.

Compound 2.16: N-(3,6-dithiaoctyl)-N'-methyl urea 6 g of methyl isocyanate in 15 ml of ethyl acetate were added dropwise at room temperature to a solution of 16.5 g of 1-amino-3,6-dithiaoctane in 40 ml of ethylacetate. The urea precipitated was recrystallised twice from methanol/water.

Yield: 12 g (43% of the theoretical).

Analysis: calc. a. $C_8H_{18}N_2OS_2$ C: 43.21; H: 8.16; S: 28.84; obsvd.: C: 43.0; H: 7.95; S: 28.70.

The thioethers according to the invention are distinguished by their high chemical stability and may be obtained easily and safely in highly pure form. They are so stable under the conditions normally prevailing during the preparation of emulsions that they do not cause any fogging, even where processing is carried out at elevated temperatures.

The thioethers according to the invention are further distinguished by the fact that they are active even in very low concentrations. Where Ostwald ripening is carried out, they support the ripening process whereas, in the normal precipitation of monodisperse emulsions, they distinctly reduce the number of nuclei.

For producing photographic silver halide emulsions by precipitating silver halides in a colloidal binder medium, the thioethers according to the invention are preferably added to the binder or to a water-soluble salt used for precipitating the silver halide, for example to the water-soluble halide, for example an alkali halide. The addition may be made for the beginning of precipitation and, at the latest, during precipitation.

The thioethers according to the invention may be used within wide pH- and pAg-ranges and over wide temperature ranges. The pH-value is generally in the range from 2 to 9 and more particularly in the range from 3 to 7; the pAg-value is generally above 6.8 and, more particularly, between 8 and 10 and the temperature range is generally from 313° K. to 358° K. and, more particularly, from 318° K. to 353° K.

The thioethers according to the invention may be used over a wide concentration range. Concentrations of from 0.05 l to 50 g and above all from 0.1 to 25 g of thioether per mole of silver halide have proved to be of particular advantage.

In one particularly preferred embodiment, the thioethers according to the invention are used together with the phosphoric acid amides known from German Offenlegungsschrift No. 2,159,379 corresponding to the formula

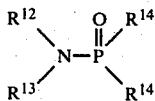

in which:

$R^{12}$ represents hydrogen, a saturated or olefinically unsaturated aliphatic group, or an aryl, cycloalkyl or acyl group;

$R^{13}$ represents hydrogen, a saturated or olefinically unsaturated aliphatic group, or an aryl or cycloalkyl group;

$R^{14}$ represents —O—$R^{15}$ or

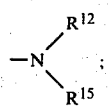

$R^{15}$ represents a saturated or olefinically unsaturated aliphatic group, aryl or cycloalkyl;
and/or with the silica sol known from German Offenlegungsschrift No. 2,015,404 which contains a water-soluble short-chain aliphatic alcohol in quantities of up to 50% by volume and/or a water-soluble organic polymer in quantities of up to 20% by weight, based on the solids content of the silica sol.

In a further embodiment of the invention the thioethers according to formula I are used as ripening additives for chemical ripening. In this embodiment a high pAg-value and a low pH-value are preferred. It is assumed that under these conditions silver ions are preferably transported to ripening centres and a controlled growth of the ripening nuclei is facilitated.

The thioethers according to the invention may be used for the production of standard silver halide emulsions. These emulsions may contain as silver halide silver chloride, silver bromide, silver iodide or mixtures thereof. The emulsions may be either negative emulsions or direct-positive emulsions. The grains of the emulsions may have a layered grain structure.

Photographic material comprising emulsions produced in the presence of the thioethers according to the invention may be developed with the usual colour developer substances, for example
N,N-dimethyl-p-phenylene diamine,
4-amino-3-methyl-N-ethyl-N-methoxyethyl aniline,
2-amino-5-diethylamino toluene,
N-butyl-N-ω-sulphobutyl-p-phenylene diamine,
2-amino-5-(N-ethyl-N-β-methane sulphonamidoethylamino)-toluene.
N-ethyl-N-β-hydroxyethyl-p-phenylene diamine,
N,N-bis-(β-hydroxyethyl)-p-phenylene diamine,
2-amino-5-(N-ethyl-N-β-hydroxyethylamino)-toluene.

Other suitable colour developers are described for example in J. Amer. Chem. Soc. 73, 3100 (1951).

Photographic material comprising emulsions produced in the presence of the thioethers according to the invention may contain the usual colour couplers which are generally incorporated in the silver halide layers themselves. Thus, the red-sensitive layer contains for example a non-diffusing colour coupler for producing the cyan component colour image, generally a phenol or α-naphthol coupler. The green-sensitive layer contains at least one non-diffusing colour coupler for producing the magenta component colour image, 5-pyrazolone or indazolone colour couplers normally being used. Finally, the blue-sensitive layer unit contains at least one non-diffusing colour coupler for producing the yellow component colour image, generally a colour coupler containing an open-chain ketomethylene group. Colour couplers of this type are known in large numbers and are described in a large number of Patent Specifications.

Reference is made here for example to the Article by W. Pelz entitled "Farbkuppler (Colour Couplers)" in "Mitteilungen aus den Forschungslaboratorien der Agfa, Leverkusen/Munchen", Vol. III (1961), and to "The Chemistry of Synthetic Dyes" by K. Venkataraman, Vol. 4, 341–387, Academic Press, 1971.

Other suitable non-diffusing colour couplers are two-equivalent couplers. Two-equivalent couplers contain a removable substituent in the coupling position, so that in contrast to the usual four-equivalent couplers they only require two equivalents of silver halide for colour coupling. Suitable two-equivalent couplers include for example the known DIR-couplers, in which the removable radical is released as a diffusing development inhibitor after reaction with colour developer oxidation products. In addition, the so-called white couplers may be used for improving the properties of the photographic material.

The non-diffusing colour couplers and dye-giving compounds are added to the photosensitive silver halide emulsions or other casting solutions by standard methods. In the case of water soluble or alkali-soluble compounds, they may be added to the emulsions in the form of aqueous solutions, to which water-miscible organic solvents, such as ethanol, acetone or dimethyl formamide may be added. If the non-diffusing colour couplers and dye-giving compounds are water-soluble or alkali-soluble compounds, they may be emulsified in known manner, for example by directly mixing a solution of these compounds in a low-boiling organic solvent with the silver halide emulsion or first with an aqueous gelatin solution, after which the organic solvent is removed in the usual way. A gelatin emulsion of the particular compound obtained in this way is then mixed with the silver halide emulsion. So-called coupler solvents or oil formers may additionally be used for emulsifying hydrophobic compounds of this type. Coupler solvents or oil formers are generally relatively high boiling organic compounds which include the non-diffusing colour couplers and development-inhibitor-releasing compounds to be emulsified in the silver halide emulsions in the form of oily droplets. In this connection, reference is made for example to U.S. Pat. Nos. 2,322,027; 2,533,514; 3,689,271; 3,764,336 and 3,765,897.

Gelatin is preferably used as binder for the photographic layers. However, it may be completely or partly replaced by other natural or synthetic binders. Examples of natural binders are alginic acid and its derivatives, such as salts, esters or amides, cellulose derivatives, such as carboxymethyl cellulose, alkyl celluloses such as hydroxyethyl cellulose, starch or its derivatives, such as ethers or esters or caragenates. Examples of synthetic binders are polyvinyl alcohol, partially hydrolysed polyvinyl acetate, polyvinyl pyrrolidone.

The emulsions may also be chemically sensitised, for example by the addition during chemical ripening of sulphur-containing compounds, for example allyl isothiocyanate, allyl thiourea and sodium thiosulphate.

Other suitable chemical sensitisers are reducing agents, for example the tin compounds described in Belgian Pat. Nos. 493,464 or 568,687, also polyamines, such as diethylene triamine, or aminoethyl sulphinic acid derivatives, for example according to Belgian Pat. No. 547,323.

Other suitable chemical sensitisers are noble metals and noble metal compounds, such as gold, platinum, palladium, irridium, ruthenium or rhodium. This method of chemical sensitisation is described in the article by R. Koslowsky in Z. Wiss. Phot. 46, 65–72, (1951).

It is also possible to sensitise the emulsions with polyalkylene oxide derivatives, for example with polyethylene oxide having a molecular weight in the range from 1000 to 20,000, with condensation products of alkylene oxides and aliphatic alcohols, glycols, cyclic dehydration products of hexitols, with alkyl-substituted phenols, aliphatic carboxylic acids, aliphatic amines, aliphatic diamines and amides. The condensation products have a molecular weight of at least 700 and preferably of more than 1000. To obtain special effects, it is of course possible to use these sensitisers in combination with one another, as described in Belgian Pat. No. 537,278 and in British Pat. No. 727,982.

The emulsions may also be optically sensitised, for example with the usual polymethine dyes, such as neutro-cyanines, basic or acid carbocyanines, rhodacyanines, hemicyanines, styryl dyes and oxonols. Stabilisers of this type are described in F. M. Hamer's book entitled "The Cyanine Dyes and Related Compounds", 1964, Interscience Publishers, John Wiley and Sons, New York.

The emulsions may contain the usual stabilisers, such as for example homopolar or salt-like compounds of mercury with aromatic of heterocyclic rings, such as mercapto-triazoles, simple mercury salts, sulphonium-mercury double salts and other mercury compounds. Other suitable stabilisers are azaindenes, preferably tetra- or pentaazaindenes, particularly those of the type substituted by hydroxyl or amino groups. Compounds of this type are described in the article by Birr in Z. Wiss. Phot. 47, (1952) 2–58. Other suitale stabilisers are inter alia heterocyclic mercapto compounds, for example phenyl mercapto tetrazole, quaternary benzthiazole derivatives and benzotriazole.

The emulsions may be hardened in the usual way, for example with formaldehyde or with halogen-substituted aldehydes containing a carboxyl group, such as mucobromic acid, diketones, methane sulphonic acid esters and dialdehydes.

The photographic layers may also be hardened with hardeners of the epoxy, heterocyclic ethylene imine or acryloyl type. Examples of hardeners such as these are described for example in German Offenlegungsschrift No. 2,263,602 or in British Pat. No. 1,266,655. It is also possible to harden the layers by the process described in German Offenlegungsschrift No. 2,218,009 to obtain colour photographic materials which are suitable for processing at high temperatures.

It is also possible to harden the photographic layers or the colour photographic multilayer materials with hardeners of the diazine, triazine or 1,2-dihydroquinoline series, as described in British Pat. Nos. 1,193,290; 1,251,091; 1,306,544 and 1,266,655; in French Pat. No. 71 02 716 or in German Patent Application No. P 23 32 317.3 (A-G 1110). Examples of hardeners such as these are diazine derivatives containing alkyl or aryl sulphonyl groups, derivatives of hydrogenated diazines or triazines such as, for example, 1,3,5-hexahydrotriazine, fluorine-substituted diazine derivatives such as, for example, fluoropyrimidine, esters of 2-substituted 1,2-dihydroquinoline or 1,2-dihydroisoquinoline-N-carboxylic acids. It is also possible to use vinyl sulphonic acid hardeners, carbodiimide or carbamoyl hardeners, as described for example in German Offenlegungsschrift Nos. 2,263,602; 2,225,230 and 1,808,685; in French Patent No. 1,491,807; in German Pat. No. 872,153 and in East German Patent No. 7218. Other suitable hardeners are described for example in British Pat. No. 1,268,550.

Emulsions according to the invention may be used for the so-called silver dye bleaching process. The present invention is also suitable for the instant image colour process and colour transfer processes. In these processes, the dyes for the partial colour images diffuse into an image receiving layer where they become firmly fixed or the colour couplers diffuse into the image receiving layer where they are reacted to form the image dye after dye-providing development.

The light-sensitive material generally contains three light-sensitive emulsion layers, each of which has a dye providing system associated with it. By "dye providing system" is meant a compound incorporated in a diffusion resistant form in the particular layer which compound is a dye or a dye precursor product which releases diffusible dyes, preferably dyes containing acid groups, under the action of oxidation products which are produced imagewise from the photographic developers when development is carried out in the presence of the alkaline processing mass. A wide variety of chemical compounds are available for use as such dye providing systems. The diffusion resistant dye providing substances according to U.S. Pat. No. 3,628,952, for example, are particularly suitable. These compounds release diffusible dyes in their reaction with oxidation products of black-and-white developers or colour developers. Another suitable class of compounds has been described in German Pat. No. 1,095,115. The compounds mentioned in the said Patent react with oxidized colour developer to produce diffusible dyes which generally belong to the class of azomethine dyes. Another suitable dye providing system has been described in U.S. Pat. No. 3,443,939 3,443,940. In this system, the release of diffusible dyes is accompanied by ring closure under the action of oxidation developer substances.

Colour transfer processes and couplers used in such processes which may also be used in the present invention have also been described in U.S. Pat. No. 3,983,606; 3,087,817; 3,185,567; 3,227,550; 3,227,551; 3,227,552; 3,227,554; 3,253,915; 3,415,644; 3,415,645 and 3,415,646.

The light-sensitive materials used for such instant colour image processes generally have the following structure:
Blue-sensitive silver halide emulsion layer;
Layer containing system releasing a magenta dye;
Separaing layer;
Red-sensitized silver halide emulsion layer;
Layer containing system releasing a cyan dye.

The invention is illustrated by the following Examples:

EXAMPLE 1

A silver bromide iodide emulsion prepared with 5 mole % of silver iodide as described in the Article by Trivelli and Smith in "The Photographic Journal", Vol. 79, May, 1939, pages 330 to 338, was used as the comparison emulsion. To prepare this emulsion, one third of the silver nitrate solution was added to the halide mixture (10% excess at the end of precipitation) over a period of 1 minute at 343° K., and, after an interval of 10 minutes, the rest of the silver nitrate solution was added over a period of 20 minutes. After precipitation, the emulsion was flocculated by adding polystyrene sulphonic acid and reducing the pH-value with mineral acid to pH 3.0, decanted and washed in order to dissolve out the excess water-soluble salts.

After redispersion at pH 7.0, the necessary quantity of gelatin was added, sodium thiosulphate and gold chloride were introduced and the emulsion ripened to maximum sensitivity at a temperature of from 323° K. to 333° K., at a pH-value of 6.0 and at a pAg-value of from 8.6 to 9.2.

The comparison emulsion then had added to it 10 ml/kg of a 5% saponin solution in water, 10 ml/kg of a 10% formaldehyde solution in water and 20 ml/kg of a 1% solution of tetraazaindene in methanol, and was cast onto a cellulose acetate substrate. The material was exposed behind a step wedge in a conventional sensitometer and was developed for 7 and 16 minutes at 293° K. in the following developer:

| | |
|---|---|
| Sodium sulphite, sicc. | 70.0 g |
| Borax | 7.0 g |
| Hydroquinone | 3.5 g |
| p-monomethylaminophenol sulphate | 3.5 g |
| Sodium citrate | 7.0 g |
| Potassium bromide | 0.4 g | made up with water to 1 liter.

In further test series, photographic emulsions were prepared and processed in the same way, except that the quantities of thioethers according to the invention indicated in Table 4 were added to the gelatin/halide solution initially introduced during precipitation. The quantitites indicated are based on the total amount of silver nitrate used.

TABLE 4

| Subst. | Thioether g/mole of AgNO$_3$ | Mean grain diameter ($\mu$) | Development 7 minutes | | | Development 16 minutes | | |
|---|---|---|---|---|---|---|---|---|
| | | | E | $\gamma$ | S | E | $\gamma$ | S |
| none (standard) | — | 2.3 | 100 | 0.95 | 0.24 | 150 | 1.00 | 0.29 |
| 2.5 | 2.8 | 1.9 | 75 | 1.20 | 0.17 | 175 | 1.60 | 0.21 |
| 2.17 | 2.8 | 2.0 | 60 | 1.10 | 0.18 | 150 | 1.30 | 0.27 |
| 2.18 | 2.8 | 1.6 | 50 | 1.10 | 0.14 | 50 | 1.20 | 0.15 |
| 2.19 | 2.8 | 1.9 | 50 | 1.00 | 0.18 | 75 | 1.30 | 1.23 |
| 1,8-dihydroxy-3,6-dithiaoctane | 2.8 | 1.7 | completely fogged after redispersion | | | | | |

E = rel. sensitivity
$\gamma$ = gradation
S = fogging.

Table 4 shows that, where the thioethers according to the invention were used, fogging was reduced and, with relatively small crystals, very high sensitivity levels were maintained in relation to the standard.

Table 4 also shows that 1,8-dihydroxy-3,6-dithiaoctane, known from German Offenlegungsschrift No. 1,904,148, resulted in complete fogging of the photographic material.

EXAMPLE 2

To produce a silver bromide iodide gelatin emulsion, the following solutions were prepared:
Solution (A)
1000 ml of water
10 g of gelatin
30 g of potassium bromide
2 g of potassium iodide Temperature 323° K.
Solution (B)
1000 ml of water
40 g of silver nitrate Temperature 318° K.

Solution (B) was uniformly poured into solution (A) over a period of 5 minutes, followed by digestion for 30 minutes at 323° K. After cooling to 293° K., 10 ml of a 10% aqueous polystyrene sulphonic acid solution were added and the pH-value was reduced to 3.0 by the addition of 25% sulphuric acid, as a result of which the emulsion flocculated out.

After settling, the supernatant solution was poured off. For chemical ripening, the flocculate was dissolved at 313° K. in 2000 ml of a 10% aqueous gelatin solution (pH 7.5).

After the flocculate had been dissolved, the pH was adjusted to 6.5, a corresponding quantity of sulphur ripener and gold salts was added, followed by ripening at 328° K. to maximum sensitivity. The emulsion had added to it 10 ml/kg of a 5% aqueous solution of saponin (wetting agent), 10 ml/kg of a 5% aqueous solution of formaldehyde (hardener) and 20 ml/kg of a 1% solution in methanol of 4hydroxy-6-methyl-1,3,3a,7-tetraazaindene (stabiliser), and was then cast onto a cellulose acetate support layer.

Further emulsions were prepared in the same way, except that the quantities of thioethers according to the invention indicated in Table 5 were added to solution (A). The quantities of thioethers indicated in Table 5 were again based on the total amount of silver nitrate used.

Exposure and further processing of these materials were carried out in the same way as in Example 1, leading to the values indicated in Table 5.

TABLE 5

| Subst. | Thio-ether g/mole of AgNO$_3$ | Mean grain diameter ($\mu$) | Development | | | | | |
|---|---|---|---|---|---|---|---|---|
| | | | 7 minutes | | | 16 minutes | | |
| | | | E | $\gamma$ | S | E | $\gamma$ | S |
| none (standard) | — | 0.50 | 100 | 1.10 | 0.18 | 130 | 1.25 | 0.23 |
| 2.5 | 2.8 | 0.25 | 175 | 1.00 | 0.05 | 200 | 1.25 | 0.08 |
| 2.17 | 2.8 | 0.35 | 200 | 1.20 | 0.07 | 230 | 1.50 | 0.15 |
| 2.19 | 2.8 | 0.30 | 175 | 0.70 | 0.05 | 175 | 1.00 | 0.23 |
| 2.18 | 2.8 | 0.40 | 130 | 0.80 | 0.14 | 150 | 0.95 | 0.23 |

E — relative sensitivity
$\gamma$ — gradation
S — fogging

EXAMPLE 3

This Example demonstrates the advantageous use of the thioethers according to the invention in the production of monodisperse emulsions.

To produce a monodisperse silver bromide emulsion, an aqueous solution of potassium bromide and an aqueous solution of silver nitrate were simultaneously added to a gelatin solution by the double jet process over a period of 32 minutes at a temperature of 343° K., at a pAg-value of 9.6 and at a pH-value of 4. In variant (A), the gelatin solution contained 1.7 g of compound 2.8 per mole of silver nitrate added. In variant (B), the gelatin solution contained 1 g of 1,8-dihydroxy-3,6-dithiaoctate per mole of silver nitrate instead of compound 2.8.

The emulsions obtained by processes (A) and (B) were similarly further processed as follows:

The emulsions were chemically ripened for 30 minutes at 343° K., by the addition of 3.3 mg of KAuCl$_4$, 80 mg of NH$_4$SCN and 1000 mg of Na$_2$S$_2$O$_3$ per mole of silver nitrate.

More silver bromide was then precipitated onto the ripened emulsion crystals obtained by the double jet process at a pAg-value of 9.9. The precipitation time was 52 minutes and the mean grain diameter of the monodisperse emulsion obtained was 0.9$\mu$. The emulsion was flocculated in the usual way, washed, redispersed in a 10% gelatin solution and then subjected to further chemical ripening for 140 minutes at pH 6.0 in the presence of 1.5 g of KAuCl$_4$, 20 mg of NH$_4$SCN and 1000 mg of Na$_2$S$_2$O$_3$ per mole of silver halide.

The emulsions obtained by processes (A) and (B) were applied separately together with the following layers onto a transparent support layer of polyester film. The sequence of the individual layers was as follows:

1. A mordant layer of gelatin (5.0 g/m$^2$) and 5.7 g/m$^2$ of a polyurethane of 4,4-diphenyl methane diisocyanate, N-ethyl diethanolamine and epichlorhydrin according to German Patent Application No. P 26 31 529.9.

2. A white pigment layer of titanium dioxide (24 g/m$^2$) and gelatin (2.4 g/m$^2$).

3. A black pigment layer of carbon black (1.9 g/m$^2$) and gelatin (2.0 g/m$^2$).

4. A dye layer containing 0.9 g/m$^2$ of the following compound:

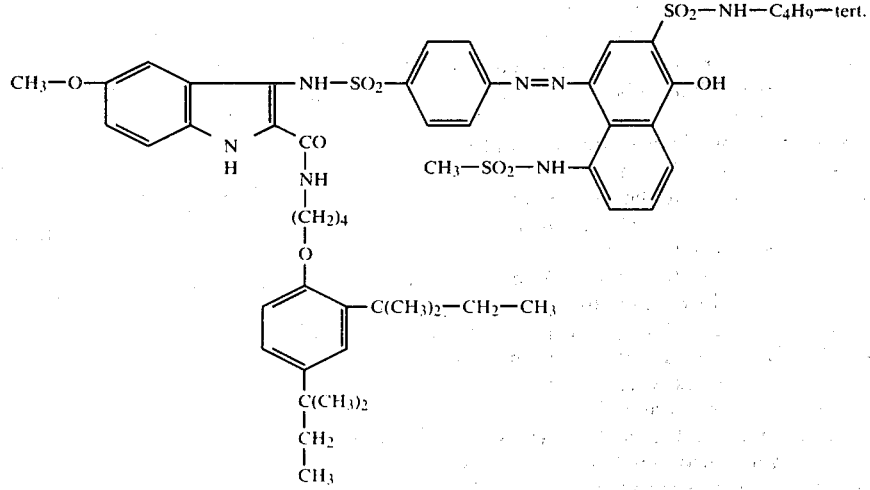

emulsified in tricresyl phosphate, and gelatin (1.0 (1.0 g/m$^2$).

5. An emulsion layer containing an emulsion obtained by process (A) or (B) described above; the emulsion was green-sensitised. The gelatin coating amounts to 1.4 g/m$^2$. The emulsion layer contains per mole of silver halide 0.066 g of octadecyl hydroquinone sulphonic acid and 3.4 mg of compound No. 32 known from German Patent Application No. P 27 46 965.4.

6. A layer of octadecyl hydroquinone sulphonic acid (1 g/m$^2$) and gelatin (1 g/m$^2$).

One sheet of each of the photosensitive materials thus produced was exposed through a grey wedge, subsequently provided with a paste container provided with a developer paste and covered on the layer side with a cover sheet of polyester film through two laterally arranged spacer strips 140μ thick. The developer paste had the following composition:

| | | |
|---|---|---|
| potassium hydroxide | 40 | g |
| benzyl alcohol | 1.5 | ml |
| p-formaldehyde | 1 | g |
| ascorbic acid | 1 | g |
| 5-methyl benzotriazole | 3 | g |
| 1-phenyl-4-methyl-4-hydroxy-methyl-3-pyrazolidone | 2 | g |
| hydroxyethyl cellulose | 35 | g | made up with water to 1000 ml.

The sandwich-like image set was passed through a pair of squeezing rollers so that the developer paste was spread out between the photosensitive part and the cover sheet. After a development time of 10 minutes, the cover sheet was removed, the image element with the paste adhering to it was neutralised and the remaining paste washed off.

A magenta-coloured positive image was obtained, far better sensitometric results being obtained with the thioethers according to the invention (process A) than with process (B):

TABLE 6

| Process | Substance | g of AgNO$_3$/m$^2$ | D$_{max}$ | D$_{min}$ | E | Q |
|---|---|---|---|---|---|---|
| A | 2.8 | 2.05 | 1.73 | 0.23 | 165 | 0.84 |
| B | 1,8-di-hydroxy-3,6-dithia-octane | 2.01 | 1.38 | 0.24 | 100 | 0.69 |

Q — quotient of D$_{max}$ and silver coating.

We claim:

1. A process for the production of photographic materials containing at least one silver halide emulsion layer, characterised in that the silver halide emulsion is produced in the presence of at least one thioether corresponding to the following formula:

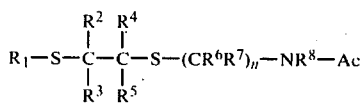

in which
R$^1$ represents an aliphatic or a cycloaliphatic or an aryl or an aralkyl radical;
R$^2$, R$^3$, R$^4$, R$^5$, R$^6$ and R$^7$ are the same of different and represent hydrogen or alkyl;
R$^8$ represents hydrogen;
Ac represents an acyl radical;
n = an integer with a value of at least 1.

2. A process as claimed in claim 1, characterised in that precipitation of the silver halide grains of the silver halide emulsion is carried out in the presence of the thioether.

3. A process as claimed in claim 1, characterised in that chemical ripening of the silver halide grains is carried out in the presence of the thioether.

4. A process as claimed in claim 2, characterised in that precipitation of the silver halide grains is additionally carried out in the presence of at least one of the following compounds:
(a) a silica sol which contains a water-soluble short-chain aliphatic alcohol in quantities of up to 50% by volume and/or a water-soluble organic polymer in quantities of up to 20% by weight, based on the solids content of the silica sol, or
(b) a phosphoric acid amide corresponding to the formula:

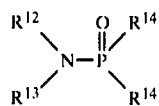

in which:
R$^{12}$ represents hydrogen, a saturated or olefinically unsaturated aliphatic group, aryl, cycloalkyl or acyl;
R$^{13}$ represents hydrogen, a saturated or olefinically unsaturated aliphatic group, aryl or cycloalkyl;
R$^{14}$ represents —O—R$^{15}$ of

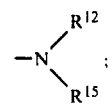

R$^{15}$ represents a saturated or olefinically unsaturated aliphatic group, aryl or cycloalkyl.

5. A process for the production of photographic materials containing at least one silver halide emulsion layer, wherein the silver halide emulsion is produced in the presence of at least one thioether corresponding to the following formula:

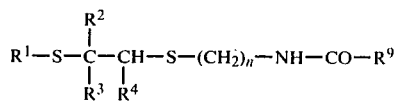

in which:
R$^1$ is an aliphatic or cycloaliphatic radical containing at most 6 carbon atoms or an aralkyl radical containing at most 8 carbon atoms;
R$^2$, R$^3$ and R$^4$ are the same or different and represent hydrogen, C$_1$-C$_7$-alkyl
n = 2 or 3;
R$^9$ represents —NH—R$^{10}$, —R$^{11}$—COOM or —R$^{11}$—SO$_3$—M;
M is a metal ion, particularly an alkali or alkaline earth metal ion;
R$^{10}$ represents hydrogen, C$_1$—C$_3$-alkyl, an alkoxy alkyl radical or an alkyl sulphonamido radical;
R$^{11}$ represents an aliphatic, cycloaliphatic or aromatic radical which may be additionally substituted and/or
R$^1$ together with R$^2$ and optionally R$^3$ represents the radical required to complete a heterocyclic ring, and/or
R$^4$ together with R$^2$ or R$^3$ represents the radical required to complete a cycloaliphatic ring.

6. A photographic material containing at least one silver halide emulsion layer which layer has been formed in the presence of a thioether corresponding to the following formula:

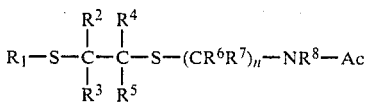

in which:
- $R^1$ represents an aliphatic or a cycloaliphatic or an aryl or an aralkyl radical;
- $R^2$, $R^3$, $R^4$, $R^5$, $R^6$ and $R^7$ are the same or different and represent hydrogen or alkyl;
- $R^8$ represents hydrogen;
- Ac represents an acyl radical, and
- n is an integer with a value of at least 1.

7. A process for the production of photographic images by exposing a photographic material containing at least one photosensitive silver halide emulsion layer to form an image, followed by development and further processing characterised in that the silver halide grains of the silver halide emulsion layer are produced in the presence of a thioether corresponding to the following formula:

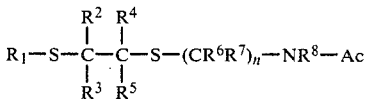

in which:
- $R^1$ represents an aliphatic or an cycloaliphatic or an aryl or an aralkyl radical;
- $R^2$, $R^3$, $R^4$, $R^5$, $R^6$ and $R^7$ are the same or different and represent hydrogen or alkyl;
- $R^8$ represents hydrogen;
- Ac represents an acyl radical, and
- n is an integer with a value of at least 1.

8. A photographic material containing at least one silver halide emulsion layer, wherein the silver halide emulsion is produced in the presence of at least one thioether corresponding to the following formula:

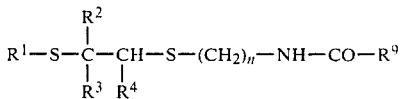

in which:
- $R^1$ represents an aliphatic or cycloaliphatic radical containing at most 6 carbon atoms or an aralkyl radical containing at most 8 carbon atoms;
- $R^2$, $R^3$ and $R^4$ may be the same or different and represent hydrogen, an alkyl radical containing from 1 to 7 carbon atoms;
- n = 2 or 3;
- $R^9$ represents $-NH-R^{10}$; $-R^{11}-COOM$ or $R^{11}-SO_3M$;
- M represents a metal ion, particularly an alkali or alkaline earch metal ion;
- $R^{10}$ represents hydrogen, an alkyl radical containing from 1 to 3 carbon atoms; an alkoxy alkyl, hydroxy alkyl, alkane sulphonyl or acyl radical;
- $R^{11}$ represents an aliphatic, cycloaliphatic or aromatic radical which may be additionally substituted, and/or
- $R^1$ together with $R^2$ and optionally $R^3$ represents the radical required to complete a heterocyclic membered ring and/or
- $R^4$ together with $R^2$ or $R^3$ represent the radical required to complete a cycloaliphatic ring, particularly a 5- or 6-membered ring.

* * * * *